United States Patent [19]

Yoshioka et al.

[11] Patent Number: 5,593,622
[45] Date of Patent: Jan. 14, 1997

[54] PREPARATION OF LIPOSOMES WITH PEG-BOUND PHOSPHOLIPID ON SURFACE

[75] Inventors: Hiroshi Yoshioka; Hiroshi Goto, both of Shizuoka-ken, Japan

[73] Assignee: Terumo Kabushiki Kaisha, Tokyo, Japan

[21] Appl. No.: 460,714

[22] Filed: Jun. 2, 1995

Related U.S. Application Data

[62] Division of Ser. No. 433,803, May 3, 1995, which is a continuation of Ser. No. 887,051, May 22, 1992, abandoned, which is a continuation of Ser. No. 802,702, Dec. 5, 1991, abandoned, which is a continuation of Ser. No. 391,952, Aug. 10, 1989, abandoned.

[30] Foreign Application Priority Data

Aug. 11, 1988 [JP] Japan ................... 63-198915
Mar. 17, 1989 [JP] Japan ................... 1-63507

[51] Int. Cl.$^6$ ................... A61K 9/127; B01J 13/22
[52] U.S. Cl. ................... 264/4.32; 264/4.3; 424/450; 428/402.2; 514/6; 514/832
[58] Field of Search ................... 424/450; 428/402.2; 514/6, 832, 833; 264/4.3, 4.32

[56] References Cited

U.S. PATENT DOCUMENTS

| | | | |
|---|---|---|---|
| 4,217,344 | 8/1980 | Vanlerberghe et al. | 424/60 |
| 4,426,330 | 1/1984 | Sears | 554/80 |
| 4,429,008 | 1/1984 | Martin et al. | 428/402.2 |
| 4,480,041 | 10/1984 | Myles et al. | 436/508 |
| 4,534,899 | 8/1985 | Sears | 554/80 |
| 4,598,051 | 7/1986 | Papahadjopoulos et al. | 436/512 |
| 4,775,991 | 10/1988 | Staudinger et al. | 378/51 |
| 4,776,991 | 10/1988 | Farmer et al. | 264/4.3 |
| 4,837,028 | 6/1989 | Allen | 424/450 |
| 4,853,228 | 8/1989 | Wallach et al. | 424/450 |
| 4,855,090 | 8/1989 | Wallach | 264/4.1 |
| 4,885,172 | 12/1989 | Bally et al. | 424/417 |
| 4,904,479 | 2/1990 | Illum | 424/490 |
| 4,915,951 | 4/1990 | Baldeschwieler et al. | 424/450 |
| 4,920,016 | 4/1990 | Allen et al. | 424/450 |
| 4,921,838 | 5/1990 | Catsimpoolas et al. | 514/25 |
| 4,931,361 | 6/1990 | Baldeschwieler et al. | 428/402.2 |
| 4,948,590 | 8/1990 | Hawrot et al. | 424/450 |
| 4,971,803 | 11/1990 | Li et al. | 424/450 |
| 5,013,556 | 5/1991 | Woodle et al. | 424/450 |

FOREIGN PATENT DOCUMENTS

| | | |
|---|---|---|
| 0072111 | 2/1983 | European Pat. Off. |
| 0118316 | 9/1984 | European Pat. Off. |
| 0140085 | 5/1985 | European Pat. Off. |
| 0220797 | 5/1987 | European Pat. Off. |
| 0043327 | 1/1992 | European Pat. Off. |
| 2552666 | 4/1985 | France . |
| 59-137409 | 8/1984 | Japan . |
| 2185397 | 7/1987 | United Kingdom . |
| 87/02777 | 5/1987 | WIPO . |
| 90/04384 | 5/1990 | WIPO . |

OTHER PUBLICATIONS

Sax et al, eds., *Hawley's Condensed Chemical Dictionary*, 11th ed. (Van Nostrand Reinhold Company, New York), p. 936 (1987).

*Primary Examiner*—Richard D. Lovering
*Attorney, Agent, or Firm*—Burns, Doane, Swecker & Mathis, LLP

[57] ABSTRACT

Agents for inhibiting adsorption of proteins on the liposome surface and liposomes which are agglutination-free by binding said inhibiting agent on the surface are disclosed. The above-mentioned inhibiting agents comprise a hydrophobic moiety and a hydrophilic macromolecular chain moiety. Adsorption of plasma proteins on the liposomes is inhibited due to the hydrophilic moiety exposed on the liposome surface with a result that agglutination of the liposomes in plasma is prevented. Therefore, there is no danger of embolism in blood vessels inhibiting blood flow when the liposomes are introduced into the living body. Accordingly, the liposomes are especially highly useful as artificial erythrocytes for which a large dose of liposomes is needed for administration.

Moreover, when liposomes are introduced into the living body, antibody protein (immunoglobulin) to the liposome which is an antigen will be adsorbed on the liposome to produce foreign body recognition in the phagocytes (macrophage) with a result that the liposome will be included in the macrophage and disappear within a short period of time. Thus, inhibition of the protein adsorption on liposome can delay disappearance of the liposome in plasma.

In addition, a method for preparing the above-described liposomes is disclosed.

18 Claims, No Drawings

PREPARATION OF LIPOSOMES WITH PEG-BOUND PHOSPHOLIPID ON SURFACE

This application is a divisional of application Ser. No. 08/433,803, filed May 3, 1995 pending, which is a continuation of application Ser. No. 07/887,051, filed May 22, 1992, now abandoned, which is a continuation of application Ser. No. 07/802,702, filed Dec. 5, 1991, now abandoned, which is a continuation of application Ser. No. 07/391,952, filed Aug. 10, 1989, now abandoned.

BACKGROUND OF THE INVENTION

1. Technical Field

The present invention relates to agents for inhibiting adsorption of proteins on the liposome surface.

Further, the invention relates to agents for preventing liposome agglutination.

Furthermore, the invention is concerned with liposomes on which adsorption of proteins is inhibited and which are agglutination-free and a method for preparing the same.

2. Prior Art

Use of liposomes as a carrier for water-soluble or fat-soluble drugs has widely been attempted (Gregoriadis, et al., Ann. N.Y. Acad. Sci., 446, 319 (1985)). Use of liposomes as artificial erythrocytes by incorporating hemoglobin, the oxygen carrier for animals, in the inner aqueous space of liposomes has also been attempted (Japanese Patent Application Laid-Open to Public 178521/1987). Liposome membrane-constituting materials of the liposomes used in these attempts, however, were those composed only of natural or synthetic lipids such as phospholipids and cholesterol.

In order to use liposomes as a carrier for drugs it is necessary to introduce the liposomes into blood vessels in the living body. However, the liposomes composed only of lipids which were conventionally employed were encountered with problems of adsorbing plasma-constituting proteins of the living body (for example, albumin, globulin and fibrinogen) which results in mutual agglutination of the liposomes. The problems were considerable especially of the liposomes which particle size exceeds 0.1 μm. Particle size of the liposomes generally employed is usually 0.1 μm–1 μm. That particle size will not be an obstacle in passing through the blood vessels in the living body because the capillary blood vessels have inner diameter as large as several μm. However, if the liposomes are agglutinated by adsorbing plasma-constituting proteins, the size of the agglutinates becomes tens of micrometers. If the agglutination occurs in the blood vessel, agglutinates of the liposomes will plug the blood vessel to inhibit blood flow possibly causing death of the living body.

Particularly when liposomes are used as artificial erythrocytes, a large dose of liposomes should be administered so that the problem of liposome agglutination in plasma was not negligible. Heretofore, however, there has been developed no technique at all for preventing the agglutination of liposomes in plasma.

In addition, when liposomes are introduced into the living body, antibody protein (immunoglobulin) to the liposome which is an antigen will be adsorbed on the liposomes to produce foreign body recognition in the phagocytes (macrophage) with a result that the liposomes will be included in the macrophage and disappear within a short period of time. Therefore, inhibition of the protein adsorption on liposomes could also delay disappearance of the liposomes in plasma.

It is also noted that the hemoglobin concentration in natural erythrocytes is approximately 30%; as the volume ratio of erythrocytes to the whole blood (hematocrit) is approximately 50%, the hemoglobin concentration in the whole blood is approximately 15%. Accordingly, in the case of artificial erythrocytes which are formed by enclosing hemoglobin in the liposome smaller in particle size than natural erythrocytes, the volume ratio of artificial erythrocytes in an artificial erythrocyte suspension will exceed 50% when the hemoglobin concentration in the artificial erythrocyte suspension is 15%, unless an aqueous solution of hemoglobin with a hemoglobin concentration of 30% or more is subjected to liposome formation. Such suspension, which is poorly fluidized, will produce adverse effects upon circulatory dynamism when administered. In this respect, it is desirable to encapsulate a large amount of hemoglobin in the inner aqueous space of liposomes using lipid in an amount as small as possible. In other words, a method for preparing artificial erythrocytes with a high encapsulation efficiency is desirable. By the dialysis method or the reverse phase method, however, it is difficult to form liposomes of an aqueous solution of hemoglobin with a higher hemoglobin concentration (30% or more) and a higher viscosity. Also by the lamina method in which a liposome-forming lipid is uniformly dissolved in an organic solvent, then the organic solvent is removed and an aqueous solution is added to the lamina of the lipid thus formed to a dispersion, the hydration and dispersion cannot easily be accomplished by the addition of an aqueous solution because the liposome-forming lipid after removal of the organic solvent has been solidified or nearly in loss of fluidity. When the aqueous solution is an aqueous solution of hemoglobin with a high concentration, the proportion of the water combined with the globin protein is high, and the amount of the free water available for hydration of the lipid is small. Thus, liposome formation at a high efficiency was difficult. Therefore, an object of the invention is to provide agents for inhibiting adsorption of proteins on the liposome surface, agents for preventing liposome agglutination, liposomes on which adsorption of proteins in plasma is inhibited and a method for preparing the same. A further object of the invention is to provide a method for preparing artificial erythrocytes comprising forming liposomes of a highly-concentrated hemoglobin at a high efficiency.

SUMMARY OF THE INVENTION

As a result of extensive studies in order to achieve the above-mentioned objects we have found that adsorption of proteins in plasma on the surface of liposomes can be prevented by incorporating a specific agent for inhibiting adsorption of proteins into lipid layer of the liposome, eventually preventing agglutination of the liposomes to each other and further facilitating hydration of the lipid even when artificial erythrocytes are prepared with an aqueous solution of hemoglobin at a high concentration thereby enabling formation of liposomes of a highly-concentrated hemoglobin at a high efficiency. The present invention was completed on the basis of the above findings.

According to the invention, there are provided agents for inhibiting adsorption of proteins on the liposome surface, agents for preventing agglutination of liposomes, liposomes containing these agents and a method for preparing the same as described below.

1) An agent for inhibiting adsorption of proteins on the liposome surface comprising a compound having a hydrophobic moiety at one end and a hydrophilic macromolecular chain moiety at the other end.

2) An agent for inhibiting adsorption of proteins on the liposome surface according to item 1 wherein the hydrophobic moiety and the hydrophilic macromolecular chain moiety are covalently bound.

3) An agent for inhibiting adsorption of proteins on the liposome surface according to item 1 wherein degree of polymerization for the hydrophilic macromolecular chain moiety is 5–1000 moles.

4) An agent for inhibiting adsorption of proteins on the liposome surface according to item 1 wherein the hydrophilic macromolecular chain moiety consists of polyethylene glycol.

5) An agent for inhibiting adsorption of proteins on the liposome surface according to item 1 wherein the hydrophobic moiety and the hydrophilic macromolecular chain moiety are bound via an ether bond.

6) An agent for inhibiting adsorption of proteins on the liposome surface according to item 5 wherein the hydrophilic macromolecular chain moiety is bound with an alcoholic radical of a long chain-aliphatic alcohol, a sterol, a polyoxypropylene alkyl or a glycerin fatty acid ester.

7) An agent for inhibiting adsorption of proteins on the liposome surface according to items 1–4 wherein the hydrophilic macromolecular chain moiety is bound with the hydrophilic group of a phospholipid.

8) An agent for inhibiting adsorption of proteins on the liposome surface according to item 7 wherein the phospholipid is phosphatidylethanolamine.

9) An agent for inhibiting adsorption of proteins on the liposome surface according to item 7 wherein the bond is formed via a triazine ring.

10) An agent for inhibiting adsorption of proteins on the liposome surface according to item 7 wherein the bond is formed via an amide bond.

11) A liposome in which the hydrophobic moiety of the agent for inhibiting adsorption of proteins on the liposome surface according to items 1–10 is fixed to the liposome membrane-constituting lipid layer and the hydrophilic macromolecular chain moiety externally extends from the liposome surface.

12) A liposome according to item 11 wherein hemoglobin is enclosed within the liposome.

13) A method for preparing liposomes on which adsorption of proteins is inhibited which comprises adding an agent for inhibiting adsorption of proteins on the liposome surface according to items 1–10 to a liposome suspension and then collecting the liposomes from said suspension.

14) A method for preparing liposomes on which adsorption of proteins is inhibited which comprises uniformly mixing an agent for inhibiting adsorption of proteins on the liposome surface with a liposome membrane-forming lipid and forming liposomes using the mixture thus obtained.

15) A liposome on which adsorption of proteins is inhibited comprising one end of a hydrophilic macromolecular chain moiety directly bound with a liposome membrane-constituting lipid and the other end externally extending from the liposome surface.

16) A method for preparing liposomes on which adsorption of proteins is inhibited which comprises adding a hydrophilic macromolecular compound activated so as to bind with a liposome membrane-constituting lipid to a liposome suspension and allowing it to react in such a way that one end of the hydrophilic macromolecule is bound with the liposome membrane-constituting lipid and the other end is extended externally from the liposome surface.

DETAILED DESCRIPTION OF THE INVENTION

The agents for inhibiting adsorption of proteins on the liposome surface or the agents for preventing agglutination of liposomes in the present invention are compounds which have a hydrophobic moiety at one end and a hydrophilic macromolecular chain moiety at the other end.

As preferred examples of the hydrophobic moiety are mentioned alcoholic radicals of a long chain aliphatic alcohol, a sterol, a polyoxypropylene alkyl or a glycerin fatty acid ester and phospholipids. As preferred examples of the hydrophilic macromolecular chain moiety are mentioned polyethylene glycols.

Especially preferable in the invention are non-ionic surface-active agents of PEG addition type in which a polyethylene glycol (called PEG hereinbelow) and an alcoholic radical of the hydrophobic moiety are bound by ether bond or PEG-bound phospholipids in which PEG and a phospholipid are covalently bound.

The polyethylene glycol-bound phospholipid in the invention is a molecule of such a structure that polyethylene glycol (PEG) is covalently bound with the hydrophilic moiety (polar head) of a phospholipid which contains one or more PEG chains per molecule. The end of the PEG chain that has not been bound with the phospholipid may also be a hydroxyl group or an ether with a short chain such as with methyl or ethyl or an ester with a short chain such as with acetic acid or lactic acid.

In order to achieve the objects of the invention, PEG chain length in the PEG-bound phospholipid molecule is desirably in the range of 5–1000 moles, more preferably 40–200 moles in terms of the average degree of polymerization. Below the above-defined range, the effect of preventing agglutination of liposomes in plasma will hardly be produced. Beyond the above-defined range, water-solubility of the PEG-bound phospholipid will be too high to be readily fixed inside the liposome membrane.

In order to produce a covalent bond between PEG and a phospholipid a reaction-active functional group is necessary at the polar moiety of the phospholipid. The functional group includes amino group of phosphatidylethanolamine, hydroxyl group of phosphatidylglycerol, carboxyl group of phosphatidylserine and the like; the amino group of phosphatidylethanolamine is preferably used.

For the formation of a covalent bond between the reaction-active functional group of a phospholipid and PEG are mentioned a method employing cyanuric chloride, a method employing a carbodiimide, a method employing an acid anhydride, a method employing glutaraldehyde and the like. The method employing cyanuric chloride (2,4,6-trichloro-striazine) is preferably used for binding the amino group of phosphatidylethanolamine with PEG. For example, treatment of monomethoxypolyethylene glycol and cyanuric chloride by known reaction procedures affords 2-O-methoxypolyethylene glycol-4,6-dichloro-s-triazine (activated PEG1 ) or 2,4-bis-(O-methoxypolyethylene glycol)-6-chloro-s-triazine (activated PEG2) {Y. Inada, et al., Chem. Lett., 7, 773–776 (1980)}. Binding of these with the amino group by a dehydrochloric acid condensation reaction yields a phospholipid with PEG covalently bound with the polar head of phosphatidylethanolamine. In the above reaction there is contained one PEG chain in one phospholipid molecule when employing activated PEG1 and two PEG chains with activated PEG2. Phospholipids bound with PEG via an amide bond is also produced by reacting monomethoxy PEG with succinic anhydride to introduce a carboxyl group into the end of the PEG and reacting the product with phosphatidylethanolamine in the presence of a carbodiimide.

In order to prepare a liposome with the PEG-bound phospholipid of the invention contained in the lipid layer, a PEG-bound phospholipid may uniformly be mixed with a liposome-forming lipid in advance, and the lipid mixture may be treated by a conventional method to form liposomes. The liposome-forming lipids as herein referred to contain as the main component phospholipids obtained from natural materials such as egg yolk and soybean or those which are produced by organic chemical synthesis used alone or in combination. Representative are phosphatidylcholine, sphingomyelin, phosphatidylethanolamine and phosphatidylserine. In addition, sterols such as cholesterol and cholestanol as a membrane-stabilizing agent, phosphatidic acid, dicetyl phosphate and higher fatty acids as a charged substance and other additives may be added. Mixing ratio of the PEG-bound phospholipid with the liposome-forming lipid is 0.1–50 mol %, preferably 0.5–20 mol % and more preferably 1–5 mol % in terms of the molar ratio to the phospholipid of the main component. Below the above-defined range, the effect of preventing agglutination of liposomes in plasma will not be sufficiently high. Beyond the above-defined range, solubilizing capacity of the PEG-bound phospholipid will cause instability of the liposome.

In effecting in advance uniform mixing of the liposome-forming lipid with the PEG-bound phospholipid, for example, the two may be dissolved in a volatile organic solvent and then the organic solvent can be removed by evaporation. If a fat-soluble drug is to be contained in the liposome, it may be mixed with the liposome-forming lipid during the above procedures. Formation of liposomes from the mixed lipids thus obtained may be carried out according to liposome formation methods usually employed. For example, any of such methods as shaking, sonication and French pressure cell may be employed. Liposomes of particle sizes between 0.1 μm and 1 μm are produced allowing for carrying a sufficient amount of a water-soluble drug or physiologically active substance in the inner aqueous space, provided that the above-mentioned PEG-bound phospholipid is used within the above-defined ranges. The PEG-bound phospholipid is contained in the lipid layer of liposomes thus obtained, but the content is not necessarily the same as that based upon the proportion originally mixed with the lipid. If the water solubility of the PEG-bound phospholipid is high, part of it will possibly be eluted into the aqueous phase outside the membrane. Although the form of the PEG-bound phospholipid present in the lipid membrane of the liposome is not clear, it is believed that the hydrophobic moiety of the PEG-bound phospholipid is present in the hydrophobic region of the liposome membrane, and the hydrophilic PEG chain is present from the hydrophilic region in the membrane over to the aqueous medium outside the membrane. It follows therefore that the PEG chain of the PEG-bound phospholipid in the liposome obtained by the method of the invention is present in both of the outer aqueous phase and the inner aqueous space of the liposome.

The PEG-bound phospholipid of the invention need not necessarily give a clear solution when dissolved in water. However, if the PEG-bound phospholipid of the invention is uniformly dissolved in water, the liposome of the invention may also be prepared by an alternative method. As a matter of fact, liposomes containing the PEG-bound phospholipid in the lipid layer may also be prepared as follows: To a suspension of liposomes carrying a water-soluble or fat-soluble drug or the like (which have been prepared by a conventionally employed liposome formation method) is added the PEG-bound phospholipid of the invention either as it is or in aqueous solution. In this case, the PEG-bound phospholipid appears to be in dispersion in the form of micelle-like molecular aggregates in the aqueous solution. When liposomes are co-existent in the dispersion, the hydrophobic moiety in the PEG-bound phospholipid molecule is fixed in the hydrophobic region in the liposome membrane by hydrophobic interaction thereby taking a structure in which the hydrophilic PEG chain is exposed on the surface of liposomes on the side of the outer aqueous phase only.

Addition of the PEG-bound phospholipid in aqueous solution may be made at the critical micelle concentration or higher. At a lower concentration, however the, amount of the phospholipid adsorbed on the liposome will not be sufficient to maintain the effect of preventing agglutination of liposomes in plasma. At a concentration which is too high, the liposome will be so unstable as eventually to cause leakage of the water-soluble drug or the like present in the inner aqueous space. Therefore, the concentration is preferably 0.01–20%, more preferably 0.05–20% in terms of the concentration in the liposome suspension.

Liposomes containing the PEG-bound phospholipid in the lipid layer can also be prepared by an alternative method. As a matter of fact, liposomes containing a phospholipid with a reaction-active functional group are prepared by a conventional method, and subsequently a PEG activated at one end is added to the outer solution of the liposomes to allow for binding with the phospholipid. For example, liposomes containing 1–50 mol % of phosphatidylethanolamine in the whole phospholipid are prepared, activated PEG2 in a basic buffer solution (pH 9 or higher) is added at a concentration of 1–20% and the mixture is allowed to react at room temperature for 1–24 hours. There is formed a structure in which the hydrophilic PEG chain is exposed on the surface on the side of the outer aqueous phase of the liposomes.

The non-ionic surface-active agent of polyoxyethylene ether addition type as referred to in the invention is a non-ionic surface active agent having a molecular structure that contains a polyoxyethylene chain as the hydrophilic moiety and in which the polyoxyethylene chain is bound with an alcoholic radical of the lipophilic (hydrophobic) moiety by an ether bond. It includes, for example, polyoxyethylene alkyl ethers, polyoxyethylene sterol ethers, polyoxyethylene alkylphenyl ethers, polyoxyethylene polyoxypropylene block polymers, polyoxyethylene polyoxypropylene alkyl ethers, polyoxyethylene glycerin fatty acid esters, polyoxyethylene sorbitan fatty acid esters and the like.

Among non-ionic surface active agents of polyoxyethylene addition type, a non-ionic surface active agent of polyoxyethylene ester addition type that has a molecular structure in which the polyoxyethylene chain is bound with the lipophilic moiety by ester bond is contained in the lipid layer of liposomes will produce a low effect in inhibiting adsorption of proteins in plasma and preventing agglutination of liposomes.

In order to achieve the objects of the invention the polyoxyethylene chain length in the non-ionic surface active agent of polyoxyethylene ether addition type is desirably in the range of 5–1000 moles, more preferably 10–40 moles in terms of the average degree of polymerization of ethylene oxide. Below the above-defined range, the effect of preventing agglutination of liposomes in plasma will hardly be developed. Beyond the above-defined range, water solubility of the non-ionic surface active agent will become too high to be readily fixed in the liposome membrane.

Among a variety of non-ionic surface active agents of polyoxyethylene ether addition type, polyoxyethylene alkyl ethers, polyoxyethylene sterol ethers, polyoxyethylene polyoxypropylene alkyl ethers and polyoxyethylene glycerin fatty acid esters are particularly effective in producing liposomes of high protein adsorption-inhibitory and agglutination-preventive effects when contained in the lipid layer of liposomes.

Polyoxyethylene alkyl ethers have a structure in which a polyoxyethylene and a saturated or unsaturated aliphatic alcohol are bound by an ether bond. Aliphatic alcohols having 8–22 carbon atoms are preferably employed.

The polyoxyethylene sterol ethers are compounds having a molecular structure in which a polyoxyethylene and a sterol are bound by an ether bond. The sterol includes animal sterols (zoosterols) such as cholesterol and cholestanol, plant sterols (phytosterols) such as sitosterol and stigmasterol and fungal sterols (mycosterols) such as ergosterol and zymosterol. Although it is not necessary to specify the nature of the sterol in the polyoxyethylene sterol esters, those which have the same structure in the side chain as that of cholesterol are preferably used.

The polyoxyethylene polyoxypropylene alkyl ethers have a molecular structure in which a polyoxypropylene is added to a saturated or unsaturated aliphatic alcohol by an ether bond, and to the end hydroxyl group of the polyoxypropylene is further added a polyoxyethylene by ether bond. Average degree of polymerization for the polyoxypropylene is preferably 2–8, and aliphatic alcohols having 8–22 carbon atoms are preferably employed.

The polyoxyethylene glycerin fatty acid esters have a molecular structure in which a polyoxyethylene is added to the free hydroxyl group of a glycerin fatty acid ester (monoglyceride or diglyceride). Either saturated or unsaturated fatty acids having 8–22 carbon atoms are preferably employed.

In order to prepare a liposome containing the non-ionic surface active agent of polyoxyethylene ether addition type in the lipid layer according to the invention, a non-ionic surface active agent of polyoxyethylene ether addition type may uniformly be mixed with a liposome-forming lipid in advance, and the lipid mixture may be treated by a conventional method to form liposomes. The liposome-forming lipid as herein referred to contains as the main component phospholipids obtained from natural materials such as egg yolk and soybean or those which are produced by organic chemical synthesis used alone or in combination. Representative are phosphatidylcholine, sphingomyelin, phosphatidylethanolamine and phosphatidylserine. In addition, sterols such as cholesterol or cholestanol as a membrane-stabilizing agent, phosphatidic acid, dicetyl phosphate and higher fatty acids as a charge-providing substance and other additives may be added. The mixing ratio of the non-ionic surface active agent of polyoxyethylene ether addition type with the liposome-forming lipid is 0.5–20 moles, preferably 1–5 moles of ethylene oxide unit per mole of the phospholipid of the main component. For example, when dipalmitoylphosphatidylcholine (molecular weight 752) as the phospholipid and polyoxyethylene phytostanol ether with an average degree of polymerization of 25 for ethylene oxide (molecular weight ca. 1500) as the non-ionic surface active agent of polyoxyethylene ether addition type are used, the molar ratio of the non-ionic surface active agent of polyoxyethylene ether addition type is 0.02–0.8 moles, preferably 0.04–0.2 moles per mole of the phospholipid, and the weight ratio is 0.04–1.6 parts by weight, preferably 0.08–0.4 parts by weight of the non-ionic surface active agent of polyoxyethylene ether addition type per part by weight of the phospholipid. Below the above-defined range, the effect of preventing agglutination of liposomes will not be sufficient. Beyond the above-defined range, the liposomes will be unstable due to the solubilizing capacity of the non-ionic surface active agent of polyoxyethylene ether addition type.

In order to effect in advance uniform mixing of a surface active agent of polyoxyethylene ether addition type with a liposome-forming lipid, for example, the two may be dissolved in a volatile organic solvent, and then the organic solvent may be removed by evaporation. If a fat-soluble drug is to be contained in the liposome, it may be mixed with the liposome-forming lipid during the above procedures. Formation of liposomes from the mixed lipids thus obtained may be carried out according to a conventional liposome formation method. For example, any of such methods as shaking, sonication and French pressure cell may be employed. Liposomes with particle sizes of 0.1–1 μm can be produced allowing for carrying a sufficient amount of a water-soluble drug or physiologically active substance in the inner aqueous space, provided that the above-mentioned non-ionic surface active agent of polyoxyethylene ether addition type is used within the above-defined range. The non-ionic surface active agent of polyoxyethylene ether addition type is contained in the lipid layer of liposomes thus obtained, but the content is not necessarily the same as that based upon the proportion originally mixed with the lipid. If water solubility of the non-ionic surface active agent of polyoxyethylene ether addition type is high, part of it will possibly be eluted into the aqueous phase outside the membrane. Although the form of the non-ionic surface active agent of polyoxyethylene ether addition type present in the lipid membrane of liposomes is not clear, it is believed that the hydrophobic moiety of the molecule of the non-ionic surface active agent of polyoxyethylene ether addition type is present in the hydrophilic region of the liposome membrane and the hydrophilic polyoxyethylene chain is present from the hydrophilic region in the membrane over to the aqueous medium outside the membrane. It follows therefore that the polyoxyethylene chain of the non-ionic surface active agent of polyoxyethylene ether addition type obtained by the method of the invention is present in both of the outer aqueous phase and the inner aqueous space of the liposome.

The non-ionic surface active agent of polyoxyethylene ether addition type of the invention need not necessarily give a clear solution when dissolved in water. However, if the non-ionic surface active agent of polyoxyethylene ether addition type of the invention is uniformly dissolved in water, the liposome of the invention may also be prepared by an alternative method. As a matter of fact, liposomes containing the non-ionic surface active agent of polyoxyethylene ether addition type of the invention in the lipid layer may also be prepared as follows: To a suspension of liposomes carrying a water-soluble or fat-soluble drug or the like (which have been prepared by a liposome formation method generally employed) is added the non-ionic surface active agent of polyoxyethylene ether addition type of the invention either as it is or in aqueous solution. In this case, the non-ionic surface active agent of polyoxyethylene ether addition type is dispersed in the form of micelles in the aqueous solution. When liposomes are co-existent in the dispersion, the hydrophobic moiety in the non-ionic surface active agent molecule of polyoxyethylene ether addition type is fixed in the hydrophobic region in the liposome membrane by hydrophobic interaction thereby taking a structure in which the hydrophilic polyoxyethylene chain is exposed on the surface of the liposome on the side of the outer aqueous phase only.

Addition of the non-ionic surface active agent of polyoxyethylene ether addition type in an aqueous solution may be made at the critical micelle concentration or higher. At a lower concentration, however, the amount adsorbed on the liposome will not be sufficient to maintain the effect of preventing agglutination of liposomes in plasma. At a too high concentration, the liposome will be so unstable as eventually to cause leakage of the water-soluble drug or the like carried in the inner aqueous space. Therefore, the concentration is preferably 0.01–5%, more preferably 0.1–2% in terms of the concentration in the liposome suspension.

When artificial erythrocytes are prepared, the mixing ratio of the non-ionic surface active agent to the liposome-forming lipid is preferably 0.5–30% by weight. Below the above-defined range, formation of hemoglobin liposomes will hardly be achieved at a high efficiency. Beyond the above-defined range, solubilizing capacity of the non-ionic surface active agent will destabilize the artificial LO erythrocytes formed.

The liposome-forming lipid used in the invention is a phospholipid obtained from natural materials such as egg yolk and soybean or those which are produced by organic chemical synthesis. They are used as the main component either alone or in combination. Representative are phosphatidylcholine (lecithin), sphingomyelin, phosphatidylethanolamine and phosphatidylserine. In addition, sterols such as cholesterol and cholestanol as a membrane-stabilizing agent, phosphatidic acid, dicetyl phosphate and higher fatty acids as a charge-providing substance and other additives may also be added.

If the phospholipid contains an unsaturated bond, there occur such special problems that lipid peroxides generated by peroxidation reaction of the unsaturated bond may be toxic, and the enclosed hemoglobin is subject to oxidative degradation. Therefore, hydrogenation products to the unsaturated group are preferably used. For example, hydrogenated egg yolk lecithin, hydrogenated soybean lecithin and the like are mentioned as hydrogenated natural phospholipid which is readily available. When such a hydrogenated natural phospholipid is employed as the main component, the phase transition temperature is as high as about 50° C. In general, liposomes are hardly formed unless the operation is carried out at the phase transition temperature or higher. However, hemoglobin will be heat degraded if formation of hemoglobin liposomes is operated at 40° C. or higher. If sterols are contained in the liposome-forming lipid, there is no definite phase transition temperature for the whole lipid mixture, and artificial erythrocytes can be prepared satisfactorily even when operated at a temperature below the phase transition temperature of the lipid main component. Higher fatty acids are preferably employed as a charge-providing substance which is usually contained in order to prevent mutual agglutination of the formed artificial erythrocytes. Adequately, mixing ratios in these liposome-forming lipids are 0.2–1 part by weight of sterols and 0.05–0.2 parts by weight of higher fatty acids per part by weight of the phospholipid.

In order to prepare a mixture of a non-ionic surface active agent and a liposome-forming lipid the two may uniformly be dissolved in a volatile organic solvent capable of uniformly dissolving the non-ionic surface active agent and the liposome-forming lipid and then the organic solvent removed by such a method as evaporation, freeze-drying or spray-drying.

In order to form artificial erythrocytes from the mixed lipid obtained, said mixed lipid may be hydrated and dispersed in an aqueous solution of hemoglobin. Whereas the hydration and dispersion may be effected merely by mechanically mixing the two, it is desirable to add high pressure-delivery treatment using such a machine as a French pressure cell. Hemoglobin concentration in the aqueous solution of hemoglobin is preferably 30–60%. Below the above-defined range, encapsulation efficiency of the hemoglobin will be low. Beyond the above-defined range, viscosity of the aqueous solution of hemoglobin will be so much increased that the hydration and dispersion will be difficult even when a non-ionic surface active agent is added.

In the method for preparing artificial erythrocytes according to the invention in which a liposome-forming lipid with hydrogenated phospholipids, sterols or higher fatty acids are mixed and an aqueous solution of hemoglobin in the above-defined range are used, there are produced almost none of the artificial erythrocytes with particle sizes of 0.01–0.03 μm having very low hemoglobin encapsulation efficiency, but for the most part, artificial erythrocytes with particle sizes of 0.1 μm or larger having high hemoglobin encapsulation efficiency.

In the lipid layer of the artificial erythrocytes thus obtained is contained the non-ionic surface active agent content of which is not necessarily the same as that based upon the initial mixing ratio with the lipid. In cases where the water solubility of the non-ionic surface active agent is high, part of it will possibly be eluted into the aqueous phase outside the membrane.

The invention will be described in more detail below with reference to Examples and Comparative Examples.

EXAMPLE 1

In 20 ml of dichloromethane were dissolved 630 mg of hydrogenated egg yolk lecithin, 317 mg of cholesterol, 53 mg of myristic acid and 150 mg of polyoxyethylene phytostanol ether (average degree of polymerization for ethylene oxide 25, BPSH 25 manufactured by Nikko Chemicals K. K.). The organic solvent was removed by evaporation. To the mixed lipid thus obtained was added 20 ml of 50% aqueous solution of hemoglobin. The mixture was blended by shaking followed by French pressure cell under a pressure of 250 kg/cm$^2$. The treatment was repeated ten times, and the liquor obtained from the treatment through French pressure cell was 1:10 diluted with physiological saline solution and subjected to centrifugal separation (17,000 r.p.m. for 30 min.). The liposome precipitates were subjected to additional centrifugal washing with two portions of 140 ml of physiological saline solution. The liposome precipitates after the washing were suspended in physiological saline solution to a hemoglobin concentration of 5%. Average particle size of the liposomes thus obtained was 0.2 μm. With 0.1 ml of the liposome suspension was mixed 0.5 ml of citrate-containing human plasma. The mixture was observed under optical microscope (×400) to find almost none of liposome agglutinates exceeding 1 μm in size.

EXAMPLE 2

In 20 ml of dichloromethane were dissolved 630 mg of hydrogenated egg yolk lecithin, 317 mg of cholesterol and 53 mg of myristic acid. The organic solvent was removed by evaporation. To the mixed lipid thus obtained was added 20 ml of 50% aqueous solution of hemoglobin. The mixture was blended by shaking followed by French pressure cell under a pressure of 500 kg/cm$^2$. The treatment was repeated ten times, and the liquor obtained was 1:10 diluted with physiological saline solution and subjected to centrifugal separation (17,000 r.p.m. for 30 min.). The liposome precipitates were subjected to additional centrifugal washing with two portions of 140 ml of physiological saline solution. The liposome precipitates after the washing were suspended in physiological saline solution to a hemoglobin concentration of 5%. Average particle size of the liposomes thus obtained was 0.2 μm. With 0.1 ml of the liposome suspension was mixed 0.5 ml of citrate-containing human plasma. The mixture was observed under optical microscope (×400) to find that the liposomes were completely agglutinated to agglutinates exceeding 50 μm in size.

To 1 ml of the above-mentioned liposome suspension adjusted to a hemoglobin concentration of 5% was added 9 ml of physiological saline solution containing 2% polyoxyethylene oleyl ether (average degree of polymerization for ethylene oxide 20). The mixture was allowed to stand at room temperature for 30 min., 1:10 diluted with physiological saline solution and subjected to centrifugal separation (17,000 r.p.m. for 30 min.). The liposome precipitates were subjected to additional centrifugal washing with two portions of 140 ml of physiological saline solution. The liposome precipitates after the washing was suspended in physiological saline solution to a hemoglobin .concentration of 5%. With 0.1 ml of the liposome suspension was mixed 0.5 ml of citrate-containing human plasma. The mixture was observed under optical microscope (×400) to find almost none of the liposome agglutinates exceeding 1 μm in size.

EXAMPLE 3

Investigations were made exactly in the same way as in Example 1 except that 150 mg of polyoxyethylene polyoxypropylene cetyl ether (average degree of polymerization for ethylene oxide 20 and for propylene oxide 8) was used in place of the polyoxyethylene phytostanol used in Example 1. There were produced the same results as in Example 1.

EXAMPLE 4

Investigations were made exactly in the same way as in Example 1 except that 150 mg of polyoxyethylene glyceryl distearate (average degree of polymerization for ethylene oxide 30) was used in place of the polyoxyethylene phytostanol used in Example 1. There were produced the same results as in Example 1.

Comparative Example 1

Investigations were made exactly in the same way as in Example 1 except that 150 mg of polyoxyethylene monostearate with an average degree of polymerization for ethylene oxide of 25 was used in place of the polyoxyethylene phytostanol ether used in Example 1. The liposomes were completely agglutinated. The agglutinates exceed 50 μm in size.

In addition, the same results were also produced with polyoxyethylene distearate (n=10 or 140).

Comparative Example 2

When polyoxyethylene monostearate was used in place of the polyoxyethylene oleyl ether used in Example 2, the liposomes were completely agglutinated. The agglutinates exceed 50 μm in size.

EXAMPLE 5

In 20 ml of dichloromethane were dissolved 1.81 g of hydrogenated egg yolk lecithin, 0.913 g of cholesterol, 0.153 g of myristic acid and 0.142 g of-polyoxyethylene phytostanol (average degree of polymerization for ethylene oxide 25, BPSH 25 manufactured by Nikko Chemicals K. K.) as a non-ionic surface active agent. The organic solvent was removed by evaporation. To the mixed lipid thus obtained was added 20 ml of 50% aqueous solution of hemoglobin. The mixture was blended by shaking followed by French pressure cell under a pressure of 250 kg/cm$^2$. The treatment was repeated ten times, and the liquor obtained was 1:10 diluted with physiological saline solution. The dilution was filtered through a filter with a pore size of 0.45 μm and then subjected to centrifugal separation (17,000 r.p.m. for 30 min.). The liposome precipitates were subjected to additional centrifugal washing with two portions of 140 ml of physiological saline solution. As the artificial erythrocytes that will be low in efficiency of hemoglobin encapsulation are not precipitated due to their low specific gravity and removed during the above operations. The artificial erythrocyte precipitates after the washing were suspended in physiological saline solution to a hemoglobin concentration of 5%. Average particle size of the artificial erythrocytes thus obtained was 0.2 μm. The entire lipid concentration in the artificial erythrocyte suspension was 33 mg/ml, and recovery ratio of the hemoglobin was 12%.

When exactly the same operations as above were conducted but without adding a non-ionic surface active agent, there were produced artificial erythrocytes with an average particle size of 0.2 μm. The entire lipid concentration in the artificial erythrocyte suspension adjusted to a hemoglobin concentration of 5% was 39 mg/ml, and recovery ratio of the hemoglobin was 7%.

EXAMPLE 6

In 50 ml of dehydrated chloroform were dissolved 150 mg of dipalmitoylphosphatidylethanolamine and 2.5 g of activated PEG2 (average molecular weight of PEG 5,000×2, manufactured by Seikagaku Kogyo K. K.). To the solution was added 2 g of sodium carbonate, and the mixture was allowed to react overnight at room temperature. After confirming completion of the reaction by disappearance of the ninhydrin color reaction the reaction mixture was filtered, and hexane was added to the filtrate for purification by re-precipitation. The purified product was dried in vacuo to obtain a PEG-bound phospholipid.

In 20 ml of dichloromethane were dissolved 630 mg of hydrogenated egg yolk lecithin, 317 mg of cholesterol, 53 mg of myristic acid and 150 mg of the above-obtained PEG-bound phospholipid. The organic solvent was removed by evaporation. To the mixed lipid thus obtained was added 20 ml of 50% aqueous solution of hemoglobin. The mixture was blended by shaking followed by French pressure cell under a pressure of 250 kg/cm$^2$. The treatment was repeated ten times, and the liquor obtained was 1:10 diluted with physiological saline solution and subjected to centrifugal separation (17,000 r.p.m. for 30 min.).

The liposome precipitates were subjected to additional centrifugal washing with two portions of 140 ml of physiological saline solution. The liposome precipitates after the washing were suspended in physiological saline solution to a hemoglobin concentration of 5%. Average particle size of the liposomes thus obtained was 0.2 μm. With 0.1 ml of the liposome suspension was mixed 0.5 ml of citrate-containing human plasma. The mixture was observed under optical microscope to find almost none of liposome agglutinates exceeding 1 μm in size.

EXAMPLE 7

In 20 ml of dichloromethane were dissolved 630 mg of hydrogenated egg yolk lecithin, 317 mg of cholesterol and 53 mg of myristic acid. The organic solvent was removed by evaporation. To the mixed lipid thus obtained was added 20 ml of 50% aqueous solution of hemoglobin. The mixture was blended by shaking followed by French pressure cell under a pressure of 500 kg/cm$^2$. The treatment was repeated ten times, and the liquor obtained was 1:10 diluted with physiological saline solution and subjected to centrifugal separation (17,000 r.p.m. for 30 min.). The liposome precipitates were subjected to additional centrifugal washing with two portions of 140 ml of physiological saline solution. The liposome precipitates after the washing were suspended in physiological saline solution to a hemoglobin concentration of 5%. Average particle size of the liposomes thus obtained was 0.2 μm. With 0.1 ml of the liposome suspension was mixed 0.5 ml of citrate-containing human plasma. The mixture was observed under optical microscope (×400) to find liposomes completely agglutinated. Size of the agglutinates exceeded 50 μm.

To 1 ml of the above-prepared liposome suspension adjusted to a hemoglobin concentration of 5% was added 9 ml of physiological saline solution containing 1% of the PEG-combined phospholipid obtained in Example 6. The mixture was allowed to stand at room temperature for 30 min., then 1:10 diluted with physiological saline solution and subjected to centrifugal separation (17,000 r.p.m. for 30 min.). The liposome precipitates were subjected to additional centrifugal washing with two portions of 140 ml of physiological saline solution. The liposome precipitates after the washing were suspended in physiological saline solution to a hemoglobin concentration of 5%. With 0.1 ml of the liposome suspension was mixed 0.5 ml of citrate-containing human plasma. The mixture was observed under optical microscope (×400) to find almost none of the liposome agglutinates exceeding 1 μm in size.

EXAMPLE 8

The same procedures as in Example 7 were repeated except that hydrogenated soybean lecithin containing 30 mol % of phosphatidylethanolamine was used in place of the hydrogenated egg yolk lecithin to obtain hemoglobin-containing liposomes. To 1 ml of a suspension of the above-prepared liposomes adjusted with 0.1M borate buffer solution (pH 10) to a hemoglobin concentration of 5% was added 100 mg of activated PEG2. The mixture was allowed to react overnight at room temperature. The reaction mixture was 1:10 diluted with physiological saline solution and subjected to centrifugal separation (17,000 r.p.m. for 30 min.). The liposome precipitates were subjected to additional centrifugal washing with two portions of 140 ml of physiological saline solution. The liposome precipitates after the washing were suspended in physiological saline solution to a hemoglobin concentration of 5%. With 0.1 ml of the liposome suspension was mixed 0.5 ml of citrate-containing human plasma. The mixture was observed under optical microscope (×400) to find almost none of the liposome agglutinates exceeding 1 μm in size.

EXAMPLE 9

To a solution of 50 g of monomethoxy PEG5000 (manufactured by Union Carbide) in 250 ml of 1,2-dichloromethane were added 5 g of succinic anhydride and 4 ml of pyridine. The mixture was boiled under reflux for 4 days. The reaction mixture was filtered, subjected to evaporation and dissolved in 100 ml of distilled water. The aqueous phase was washed with ether and then extracted with 100 ml of chloroform. After evaporated the residue was recrystallized from ethyl acetate to give monocarboxy-terminated PEG. In 30 ml of chloroform were dissolved 725 mg of the PEG, 100 mg of dipalmitoylphosphatidylethanolamine and 30 mg of dicyclohexylcarbodiimide. The solution was allowed to react overnight at 50° C. The reaction mixture was subjected to re-precipitation with 300 ml of hexane. There was obtained phospholipid bound via amide bond with PEG. The same results as in Examples 6 and 7 were produced in an experiment using the phospholipid.

What is claimed is:

1. A process for the preparation of a liposome comprising PEG-bound phospholipid on the surface thereof, wherein said PEG-bound phospholipid extends outwardly, and does not substantially extend inwardly from the surface of said liposome, said process comprising preparing a liposome and adding PEG-bound phospholipid to said liposome thereby fixing the PEG-bound phospholipid on the surface of said liposome.

2. The process according to claim 1, wherein the amount of said PEG-bound phospholipid is 0.1 to 50 mol % based on the molar ratio of the phospholipid of said liposome.

3. The process according to claim 2, wherein the amount of said PEG-bound phospholipid is 0.5 to 20 mol % based on the molar ratio of the phospholipid of said liposome.

4. The process according to claim 3, wherein the amount of said PEG-bound phospholipid is 1 to 5 mol % based on the molar ratio of the phospholipid of said liposome.

5. The process according to claim 1, wherein said liposome has an average particle size of 0.1 to 1 micron.

6. The process according to claim 1, wherein the PEG chain length of said PEG-bound phospholipid is in the range of 5 to 1000 moles in terms of the average degree of polymerization.

7. The process according to claim 6, wherein the PEG chain length of said PEG-bound phospholipid is in the range of 40 to 200 moles in terms of the average degree of polymerization.

8. The process according to claim 1, wherein the phospholipid of said PEG-bound phospholipid is phosphatidylcholine, sphingomyelin, phosphatidylethanolamine or phosphatidylserine.

9. The process according to claim 8, wherein the phospholipid of said PEG-bound phospholipid is phosphatidylethanolamine.

10. A process for the preparation of a liposome comprising PEG-bound phospholipid on the surface thereof, wherein said PEG-bound phospholipid extends outwardly and does not substantially extend inwardly from the surface of said liposome, said process comprising preparing a liposome containing a phospholipid with a reaction-active functional group and adding PEG which is activated at one end to said liposome thereby allowing the PEG to couple with the phospholipid of said liposome.

11. The process according to claim 10, wherein the amount of said PEG-bound phospholipid is 0.1 to 50 mol % based on the molar ratio of the phospholipid of said liposome.

12. The process according to claim 11, wherein the amount of said PEG-bound phospholipid is 0.5 to 20 mol % based on the molar ratio of the phospholipid of said liposome.

13. The process according to claim 12, wherein the amount of said PEG-bound phospholipid is 1 to 5 mol % based on the molar ratio of the phospholipid of said liposome.

14. The process according to claim 10, wherein said liposome has an average particle size of 0.1 to 1 micron.

15. The process according to claim 10, wherein the PEG chain length of said PEG-bound phospholipid is in the range of 5 to 1000 moles in terms of the average degree of polymerization.

16. The process according to claim 15, wherein the PEG chain length of said PEG-bound phospholipid is in the range of 40 to 200 moles in terms of the average degree of polymerization.

17. The process according to claim 10, wherein the phospholipid of said PEG-bound phospholipid is phosphatidylcholine, sphingomyelin, phosphatidylethanolamine or phosphatidylserine.

18. The process according to claim 17, wherein the phospholipid of said PEG-bound phospholipid is phosphatidylethanolamine.

* * * * *

UNITED STATES PATENT AND TRADEMARK OFFICE
CERTIFICATE OF CORRECTION

PATENT NO. : 5,593,622
DATED : January 14, 1997
INVENTOR(S) : Hiroshi YOSHIOKA et al It is certified that error appears in the above-indentified patent and that said Letters Patent is hereby corrected as shown below:

In Column 9, line 28, delete "LO".

Signed and Sealed this

First Day of April, 1997

Attest:

BRUCE LEHMAN

Attesting Officer     *Commissioner of Patents and Trademarks*